United States Patent
Dalla Pria

(10) Patent No.: US 7,169,184 B2
(45) Date of Patent: Jan. 30, 2007

(54) INVERSE PROSTHESIS FOR THE ARTICULATION OF THE SHOULDER

(75) Inventor: Paolo Dalla Pria, Udine (IT)

(73) Assignee: Lima LTO SPA, Villanova di San Daniele del Friuli (IT)

( * ) Notice: Subject to any disclaimer, the term of this patent is extended or adjusted under 35 U.S.C. 154(b) by 99 days.

(21) Appl. No.: 10/833,325

(22) Filed: Apr. 28, 2004

(65) Prior Publication Data

US 2004/0220673 A1 Nov. 4, 2004

(30) Foreign Application Priority Data

Apr. 30, 2003 (IT) .......................... UD2003A0094

(51) Int. Cl.
*A61F 2/40* (2006.01)
(52) U.S. Cl. .................. 623/19.12; 623/19.13
(58) Field of Classification Search ............ 623/19.11, 623/19.12, 19.13, 19.14, 22.11, 23.11, 23.42
See application file for complete search history.

(56) References Cited

U.S. PATENT DOCUMENTS

| | | |
|---|---|---|
| 5,702,447 A | 12/1997 | Walch et al. |
| 6,197,062 B1 | 3/2001 | Fenlin |
| 6,790,234 B1 * | 9/2004 | Frankle ................... 623/19.12 |
| 2003/0114933 A1 | 6/2003 | Bouteens et al. |

FOREIGN PATENT DOCUMENTS

| | | |
|---|---|---|
| DE | 20022306 | 7/2001 |
| DE | 20207913 | 10/2002 |
| EP | 0776636 | 6/1997 |
| EP | 1064890 | 1/2001 |
| EP | 1064890 A1 * | 1/2001 |
| FR | 2704747 | 11/1994 |
| FR | 2737107 | 1/1997 |
| WO | 0041653 | 7/2000 |
| WO | WO 0147442 A1 * | 12/2000 |
| WO | 0147442 | 7/2001 |

* cited by examiner

*Primary Examiner*—Eduardo C. Robert
*Assistant Examiner*—James L. Swiger
(74) *Attorney, Agent, or Firm*—Stevens, Davis, Miller & Mosher, LLP

(57) ABSTRACT

Inverse prosthesis of the shoulder for the articulation of a humerus in a scapula of a shoulder comprising a glenoid cavity. The prosthesis includes an at least partly convex articulation element, including elements for support and attachment to the glenoid cavity, and able to articulate with an at least partly concave mating articulation element, associated with the top of the humerus. The articulation element includes a substantially hemi-spherical element and a pin-type implant element made as distinct and reciprocally removable elements, so as to allow them to be assembled sequentially with respect to the glenoid cavity.

14 Claims, 2 Drawing Sheets

INVERSE PROSTHESIS FOR THE ARTICULATION OF THE SHOULDER

FIELD OF THE INVENTION

The present invention concerns a prosthesis of the shoulder for the articulation of the head of a humerus with respect to the relative scapula. To be more exact, the prosthesis of the shoulder according to the invention is configured as an inverse prosthesis, wherein a convex shaped head is associated with the glenoid cavity and articulates in an artificial concave seating associated with the top of the humerus.

BACKGROUND OF THE INVENTION

Inverse prostheses of the shoulder are known, for the articulation of a sphere attached to the scapula in a mating cavity obtained in the upper part of the humerus, which inversely reproduce the gleno-humeral anatomy. Normally, inverse prostheses are used in the event of serious muscular degeneration of the shoulder, particularly of the rotator cuff muscles. The degeneration of such muscles causes a prevalent action by the deltoid, which tends to draw the humerus upwards, consequently making the humeral bone head, or possible artificial head, move upwards, with the risk of making it knock against the protrusion which prolongs the spine of the scapula, known as acromion.

Starting from the idea of eliminating the humeral head, inverse prostheses comprise, as elements associated with the humerus, a concave shaped humeral seating including a relative attachment shaft implanted in the humerus.

The humeral seating defines the articulation for a spherical body attached to the glenoid cavity, which is provided in a single body with a pin for direct attachment in the glenoid cavity, or to a support previously attached to said glenoid cavity.

One shortcoming of known inverse prostheses is that the attachment pin of the aforementioned spherical body is difficult to insert into the glenoid cavity, or into the relative support element, previously applied, due to the extremely limited spaces available; this is an obstacle to precise positioning and a limit to the surgeon's operating possibilities.

A further disadvantage of known inverse prostheses is that the position of the spherical body cannot be oriented or translated as desired with respect to the wall of the glenoid cavity where the relative pin is attached.

One purpose of the invention is to achieve a prosthesis for the articulation of the shoulder wherein the implantation of an inverse prosthesis will allow the spherical body to be assembled easily and precisely in the glenoid cavity, facilitating the work of the surgeon.

Another purpose of the invention is to achieve a prosthesis of the shoulder in an inverse configuration wherein it is possible to select the orientation and position of the spherical body with respect to its axis of implantation in the glenoid cavity, in relation to the presence of non-regular spaces between the glenoid cavity and the head of the humerus.

The Applicant has devised, tested and embodied the present invention to achieve these purposes and other advantages, and to overcome the shortcomings of the state of the art.

SUMMARY OF THE INVENTION

The present invention is set forth and characterized in the main claim, while the dependent claims describe other innovative characteristics of the invention.

An inverse prosthesis of the shoulder comprises an at least partly convex articulation element associated with relative implant means, normally a pin defining an implantation axis, for attachment to the glenoid cavity, and able to articulate with a mating articulation element, at least partly concave, associated with the top of the humerus. According to the invention, the articulation element associated with the glenoid cavity, and the relative pin-type implant means, are made as distinct elements and are reciprocally removable, so as to allow them to be assembled sequentially with respect to the glenoid cavity.

Thanks to this, according to a first feature, the articulation element and the pin-type implant means can also be made of different materials; the articulation element can be made for example of ceramic, or of metal such as for example a cobalt-based alloy, while the pin-type implant element can be made of a different metal such as for example a titanium-based alloy.

Using a ceramic material or a cobalt-based alloy improves the resistance to wear of the convex element, which functions as the articulation element, while using a titanium-based alloy ensures both good bone integration and also the due and necessary resistance of the anchorage.

Moreover, the size of the elements can also be selected on each occasion according to the space available in the glenoid cavity of the patient's scapula.

According to another feature, using a pin distinct from the relative convex articulation element allows the surgeon, during the implantation step, to orientate the pin as desired in the space with respect to its axis of insertion, without constraints created by the lack of space available.

In a subsequent step, after having anchored the pin to the bone seating of the glenoid or to a relative support element, the convex articulation element can be associated, with the desired orientation, with the relative pin-type implant element.

The coupling of the articulation element and the relative pin-type implant means can be of any type, for example conical coupling, by means of screwing, with auxiliary elements such as rivets or pins or other.

According to another characteristic feature of the invention, the articulation element has a convex surface with at least an axis of symmetry, and the pin-type implant means are able to be positioned in an eccentric or angled position with respect to such axis of symmetry. The eccentricity or angulation of the implant means with respect to the articulation element allows to translate or orient the articulation element itself with respect to the glenoid cavity, especially when the bone tissue of the glenoid is not healthy and it is necessary to move the point of implantation.

According to a variant, if the prosthesis according to the invention comprises a support element previously attached to the glenoid cavity, the coupling of the pin-type implant means and the support element solid with the bone seating is of the conical type.

According to a variant, the pin-type implant means are able to be screwed at least partly into the glenoid support element.

BRIEF DESCRIPTION OF THE DRAWINGS

These and other characteristics of the present invention will become apparent from the following description of a preferential form of embodiment, given as a non-restrictive example with reference to the attached drawings wherein.

DETAILED DESCRIPTION OF A PREFERENTIAL FORM OF EMBODIMENT OF THE INVENTION

Figure 1:
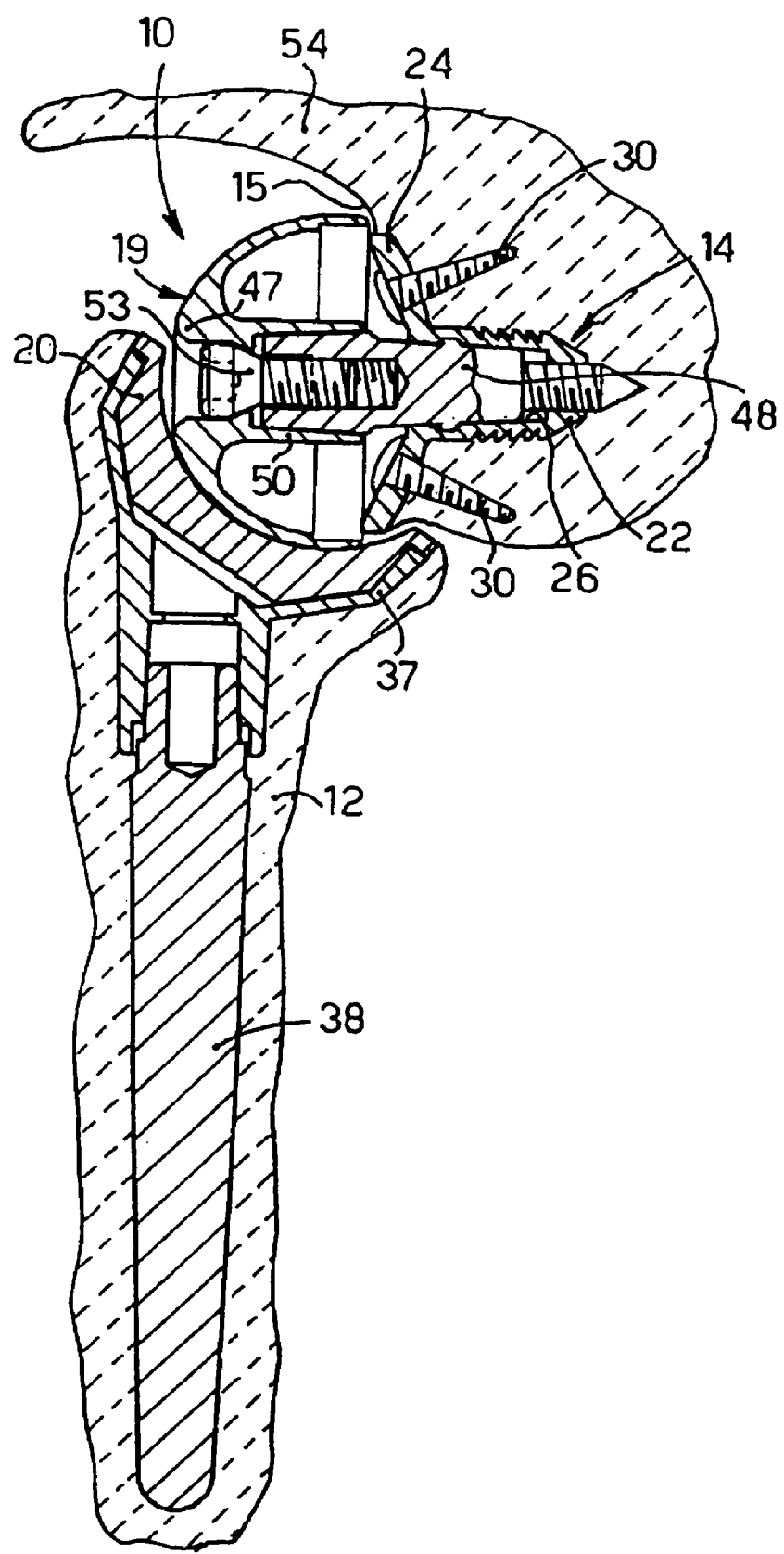
FIG. 1 is a longitudinal section of an inverse type prosthesis according to the invention.

With reference to the attached drawings, the reference number 10 denotes an inverse prosthesis according to the present invention, able to be implanted in a shoulder in order to allow the articulation of a humerus 12 in a relative glenoid cavity 15 of a scapula 54, only partly shown.

The prosthesis 10 comprises a support element 14, or glenoid element, which is first anchored to the glenoid 15, and is made of metal or, according to a variant, of plastic.

The support element 14 (FIG. 2) comprises a shaft 22 and a plate 24, coaxial with the shaft 22 and having a substantially concave outer surface 25 or, according to a variant, substantially plane.

A convex or spherical articulation element, solid with the glenoid 15, is anchored to said support element 14, as will be described hereafter.

The support element 14 is also provided with a central hole 26, in this case with a conical section, which is through and, with variations in diameter, passes through the plate 24 and the shaft 22; the element 14 also has a plurality of holes 28, arranged peripherally with respect to the central hole 26, for the insertion of attachment screws 30 to attach the support element 14 to the wall of the bone seating.

The support element 14 is implanted by forcing the shaft 22 through interference, by screwing or cementing it into a mating seating made in the glenoid 15, and the attachment screws 30 are subsequently screwed in.

According to a variant not shown in the drawings, the shaft 22 is sectioned longitudinally into two identical sub-portions for reasons of elasticity and stable attachment.

A spherical body, or glenoid head 19, is applied on the support element 14, which allows the articulation of a concave articulation element solid with the humerus 12.

To be more exact, the articulation element solid with the humerus 12 comprises an anchoring shaft 38, which can be inserted into the humerus 12 by percussion or by screwing, and may or may not be cemented to the bone.

In this case, a humeral cup 20 (FIG. 1) is associated with the shaft 38.

To be more exact, a mating supporting humeral body 37 is provided to attach the humeral cup 20.

The glenoid head 19 (FIGS. 1 and 2) comprises in this case a hemi-spherical head 47, with an axis of symmetry Y, and a coupling pin 48, which is able to be inserted and coupled, in this case by means of conical coupling as will be described in more detail hereafter, into the central hole 26 of the glenoid support element 14.

According to a variant, not shown in the drawings, the pin 48 is completely threaded, and is able to be screwed into a central hole 26, suitably threaded inside.

According to a characteristic of the present invention, the pin 48 is a distinct component with respect to the hemi-spherical head 47. In this way, the pin 48 can be assembled separately, in a first operating step, onto the support element 14 and subsequently, in a second step, the hemi-spherical head 47 can easily be attached on the pin 48.

The fact that the pin 48 and the hemi-spherical head 47 are made in several parts, first of all, facilitates the insertion and positioning of the glenoid head 19 on the support element 14, since it allows, even when there are very limited spaces available to the surgeon, to orientate the pin 48 as desired in the space with respect to its axis of implantation.

Secondly, the pin 48 and the hemi-spherical head 47 can be made of different materials.

The pin 48 can be made of a titanium alloy to ensure the due resistance and a sufficient bone integration, while the hemi-spherical head 47 is made of an alloy based on cobalt-chrome-molybdenum, or of ceramic material, in order to improve the resistance to wear of the prosthesis 10. To be more exact, the ceramic material is used for those cases where the patients are allergic to certain elements contained in cobalt-based alloys.

The hemi-spherical head 47 in this case is hollow inside, both for reasons of weight and also so as not to interfere with the head portions of the attachment screws 30.

The pin 48 (FIG. 2) comprises a first conical portion 48a in which an internally threaded cavity 49 is made, and a second conical portion 48b, able to be inserted into the central hole 26 of the support element 14 and having an opposite taper with respect to the first portion 48a.

Figure 2:
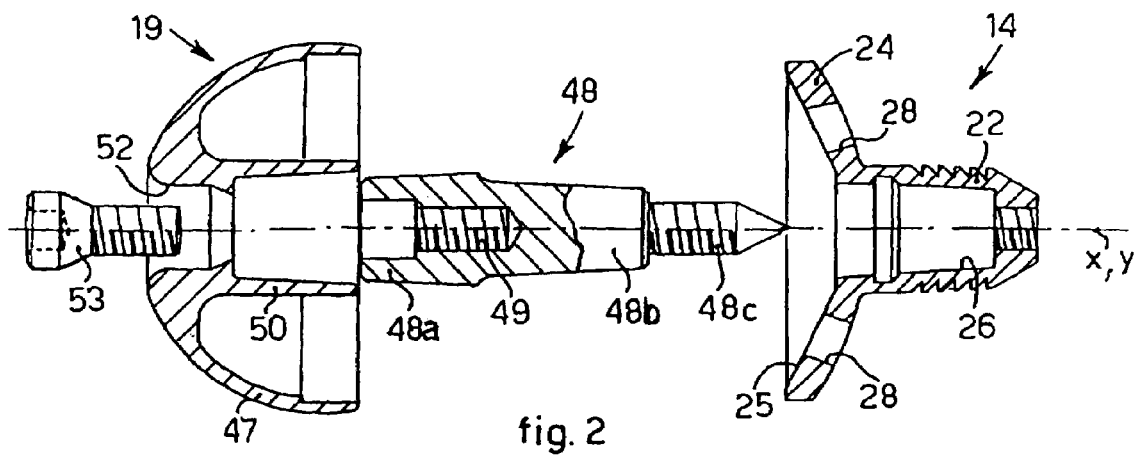
FIG. 2 shows an exploded detail of the prosthesis in FIG. 1.

The pin 48 can have, in one embodiment, a length greater than the shaft 22 and also comprises, in the embodiment shown here, a threaded terminal portion 48c, able to be screwed into the terminal portion of the shaft 22 and into the bone wall of the scapula 54, in order to attach the pin 48 definitively when the latter is assembled and clamped into the hole 26 of the support element 14 (FIG. 2).

On the inner side of the hemi-spherical head 47 a coupling cone 50 is made in one piece therewith, and extends towards the outside; inside it a through cavity 52 is made, open towards the outside.

The cone 50 serves to implant the head 47 onto the corresponding conical portion 48a of the pin 48, after the latter has been clamped onto the support element 14.

Alternatively, the pin 48 and the head 47 can be previously pre-assembled and attached to the support element 14 by screwing the portion 48c.

As a last step, the hemi-spherical head 47 is clamped to the pin 48 by means of a safety attachment screw 53, which is inserted through the open cavity 52 and screwed into the threaded cavity 49 of the first conical portion 48a.

In the embodiment shown in FIG. 2, the main axis of symmetry Y of the hemi-spherical head 47 coincides with an axis X of the cone 50 by coupling with the pin 48.

Figure 3:
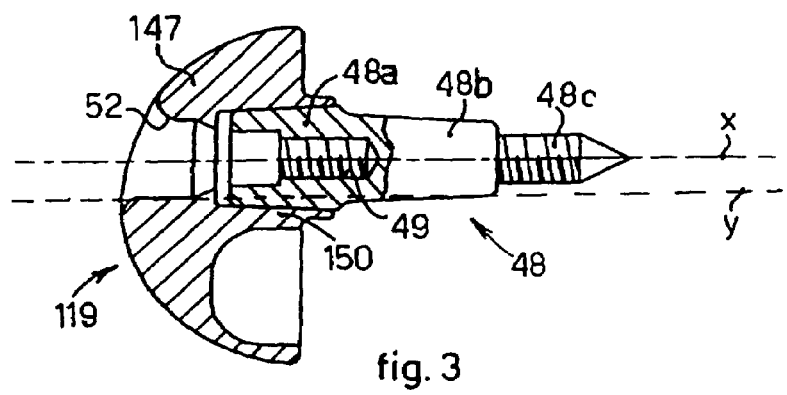
FIG. 3 shows a variant of FIG. 2.

According to the variant shown in FIG. 3, a glenoid head 119 comprises a hemi-spherical head 147, having a convex surface symmetrical with respect to an axis Y, and which is coupled by means of a relative cone 150 with a pin 48 which has an axis X of implantation, eccentric with respect to the axis of symmetry Y.

The eccentricity of the coupling cone 150 allows to translate the hemi-spherical head 147 in a front-rear or lateral-medial direction with respect to the glenoid 15, or to modify its orientation with respect to the shaft 22. This allows to correct possible non-symmetrical spaces, especially in the event that the bone wall of the glenoid 15 is not healthy, and the shaft 22 has to be implanted in a slightly translated position with respect to the zone where the glenoid head 19 articulates with the humeral cup 20.

It is clear, however, that modifications and/or additions of parts may be made to the universal prosthesis 10 as described heretofore, without departing from the field and scope of the present invention.

For example, the axis X of the coupling cone 150 can be angled with respect to the axis of symmetry Y.

The invention claimed is:

1. Inverse prosthesis of the shoulder for the articulation of a humerus in a scapula of a shoulder having a glenoid cavity, comprising:
   an at least partly convex articulation element, including means for support and attachment of the prosthesis to said glenoid cavity, and able to articulate with an at least partly concave mating articulation element, associated with the top of said humerus,
   wherein said partly convex articulation element comprises a substantially hemi-spherical element having a hemi-spherical head and said means for support and attachment of said partly convex articulation element comprises a pin-type implant element made as distinct and reciprocally removable elements so that said hemi-spherical element is removably attachable onto said pin-type element, said pin-type element includes a distal end and a proximal end relative to the hemi-spherical head,
   wherein the substantially hemi-spherical element and said pin-type implant element are assembleable sequentially with respect to said glenoid cavity,
   wherein the means for support and attachment of said partly convex articulation element comprises a support element, and
   wherein said pin-type implant element includes a first conical portion, for coupling with said substantially hemi-spherical articulation element, and a second conical portion for coupling with a mating conical portion of the support element for functionally attaching to said glenoid cavity, said first conical portion and said second conical portion tapering in opposite directions;
   wherein the first conical portion has a first end and a second end, the first conical portion first end having a width wider than a width of the first conical portion second end, wherein the first conical portion tapers to narrow from the first conical portion first end to the first conical portion second end;
   wherein the second conical portion has a first end and a second end, the second conical portion first end having a width wider than a width of the second conical portion second end, wherein the second conical portion tapers to narrow from the second conical portion first end to the second conical portion second end; and
   wherein the first conical portion tapers towards the proximal end and the second conical portion tapers towards the distal end.

2. Prosthesis of the shoulder as in claim 1, wherein said substantially hemi-spherical articulation element is at least partly hollow inside, and is provided on the hollow side with a coupling means able to be associated with a mating conical portion of said pin-type implant element.

3. Prosthesis of the shoulder as in claim 2, wherein said coupling means comprise a conical element hollow inside and able to be coupled by means of conical coupling with said conical portion of said pin-type implant element.

4. Prosthesis of the shoulder as in claim 2, wherein said coupling means are offset and/or angled with respect to an axis of symmetry of said substantially hemi-spherical element.

5. Prosthesis of the shoulder as in claim 1, wherein said pin-type implant element has a threaded terminal portion screwball into said glenoid cavity.

6. Prosthesis of the shoulder as in claim 1, wherein said substantially hemi-spherical element and said pin-type implant element are made of different materials.

7. Prosthesis of the shoulder as in claim 6, wherein said substantially hemi-spherical element is made of a first material comprising one of a ceramic material and a metal, and
   said pin-type implant element is made of a second material comprising a metal,
   wherein when said first material comprises metal, the metal of said second material is different from the metal of said first material.

8. Prosthesis of the shoulder as in claim 1, wherein the convex surface of said substantially hemi-spherical element is symmetrical at least with respect to an axis, wherein said pin-type implant element positionable in an eccentric position with respect to said axis of symmetry of said substantially hemi-spherical element.

9. Prosthesis of the shoulder as in claim 8,
   wherein said substantially hemi-spherical articulation element is at least partly hollow inside, and is provided on the hollow side with a coupling means able to be associated with a mating conical portion of said pin-type implant element; and
   wherein said coupling means are offset and/or angled with respect to an axis of symmetry of said substantially hemi-spherical element.

10. Prosthesis of the shoulder as in claim 1, wherein the convex surface of said substantially hemi-spherical element is symmetrical at least with respect to an axis, wherein said pin-type implant element is positionable along an axis inclined with respect to the axis of symmetry of said articulation element.

11. Prosthesis of the shoulder as in claim 1, comprising at least a support element adapted for attachment to said glenoid cavity and provided with a coupling means for the attachment of said pin-type implant element of said partly convex articulation element,
   wherein at least one portion of said pin-type implant element is attachable to a mating portion of said coupling means by means of conical coupling.

12. An inverse prosthesis of the shoulder for the articulation of a humerus in a scapula of a shoulder having a glenoid cavity, comprising:
   an at least partly convex articulation element, including means for support and attachment of the prosthesis to said glenoid cavity, and able to articulate with an at least partly concave mating articulation element, associated with the top of said humerus,
   wherein said partly convex articulation element comprises a substantially hemi-spherical element and a pin-type implant element made as distinct and reciprocally removable elements, so as to allow the substantially hemi-spherical element and said pin-type implant element to be assembled sequentially with respect to said glenoid cavity,
   wherein said substantially hemi-spherical articulation element is at least partly hollow inside, and is provided on the hollow side with a coupling means able to be associated with a mating conical portion of said pin-type implant element, and
   wherein said coupling means comprise a conical element hollow inside and able to be coupled by means of conical coupling with said conical portion of said pin-type implant element, and
   wherein said conical element extends as far as a convex outer side of said substantially hemi-spherical element defining a through cavity.

13. An inverse prosthesis of the shoulder for the articulation of a humerus in a scapula of a shoulder having a glenoid cavity, comprising:

an at least partly convex articulation element, including means for support and attachment of the prosthesis to said glenoid cavity, and able to articulate with an at least partly concave mating articulation element, associated with the top of said humerus, wherein said partly convex articulation element comprises a substantially hemi-spherical element and a pin-type implant element made as distinct and reciprocally removable elements, so as to allow the substantially hemi-spherical element and said pin-type implant element to be assembled sequentially with respect to said glenoid cavity, wherein in said pin-type implant element a threaded cavity is made for screwing in a safety screw to attach the pin-type implant element to said substantially hemi-spherical element.

14. An inverse prosthesis of the shoulder for the articulation of a humerus in a scapula of a shoulder having a glenoid cavity, comprising:

an at least partly convex articulation element, including means for support and attachment of the prosthesis to said glenoid cavity, and able to articulate with an at least partly concave mating articulation element, associated with the top of said humerus, wherein said partly convex articulation element comprises a substantially hemi-spherical element and a pin-type implant element made as distinct and reciprocally removable elements, so as to allow the substantially hemi-spherical element and said pin-type implant element to be assembled sequentially with respect to said glenoid cavity, the prosthesis further comprising at least a support element adapted for attachment to said glenoid cavity and provided with a coupling means for the attachment of said pin-type implant element, wherein at least one portion of said pin-type implant element is adapted for attachment to a mating portion of said coupling means by means of conical coupling;

wherein at least a terminal portion of said pin-type implant element is able to be attached to a mating portion of said coupling means by means of screwing.

* * * * *